United States Patent [19]

Iwamoto et al.

[11] Patent Number: 5,502,033

[45] Date of Patent: *Mar. 26, 1996

[54] NEW ANTIMICROBIAL POLYPEPTIDE COMPOUND A PHARMACEUTICAL COMPOSITION COMPRISING THE SAME, AND A METHOD FOR TREATING INFECTIOUS DISEASES

[75] Inventors: Toshiro Iwamoto, Tsukuba; Akihiko Fujie; Kumiko Nitta, both of Tsuchiura; Yasuhisa Tsurumi; Nobuharu Shigematsu, both of Tsukuba; Chiyoshi Kasahara, Ikeda; Motohiro Hino, Tsuchiura; Masakuni Okuhara, Tsukuba, all of Japan

[73] Assignee: Fujisawa Pharmaceutical Co., Ltd., Osaka, Japan

[*] Notice: The term of this patent shall not extend beyond the expiratin date of Pat. No. 5,376,634.

[21] Appl. No.: 218,883

[22] Filed: Mar. 28, 1994

Related U.S. Application Data

[63] Continuation of Ser. No. 610,759, Nov. 8, 1990, abandoned.

[30] Foreign Application Priority Data

Nov. 13, 1989 [GB] United Kingdom ............ 8925593

[51] Int. Cl.$^6$ ............ A61K 38/00; C07K 5/12; C07K 7/06; C07K 7/00
[52] U.S. Cl. ............ 514/11; 514/9; 530/317
[58] Field of Search ............ 530/317, 329; 514/9, 11, 17

[56] References Cited

U.S. PATENT DOCUMENTS

| | | | |
|---|---|---|---|
| 4,287,120 | 9/1981 | Abbott et al. | 530/317 |
| 4,320,052 | 3/1982 | Abbott et al. | 530/317 |
| 4,320,053 | 3/1982 | Abbott et al. | 530/317 |
| 4,322,338 | 3/1982 | Abbott et al. | 530/317 |
| 5,376,634 | 12/1994 | Iwamoto et al. | 530/317 |

FOREIGN PATENT DOCUMENTS

| | | |
|---|---|---|
| 031662 | 7/1981 | European Pat. Off. . |
| 311193 | 4/1989 | European Pat. Off. . |
| 0448354 | 3/1990 | European Pat. Off. . |
| 0359529 | 3/1990 | European Pat. Off. . |
| 2066263 | 8/1981 | United Kingdom . |

OTHER PUBLICATIONS

Schmatz, et al, *Proc. Natl. Acad Sci*, vol. 87, pp. 5950–5954, 1990.

*Primary Examiner*—Jill Warden
*Assistant Examiner*—S. G. Marshall
*Attorney, Agent, or Firm*—Oblon, Spivak, McClelland, Maier, & Neustadt

[57] ABSTRACT

A compound having antimicrobial activity of the following general formula:

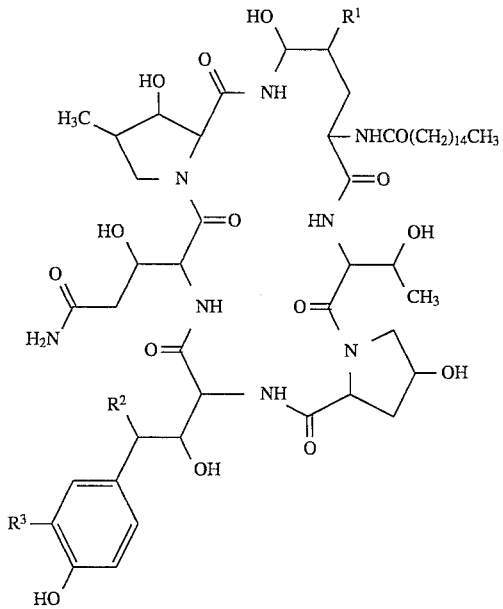

wherein $R^1$ is hydrogen or hydroxy, $R^2$ is hydrogen or hydroxy, $R^3$ is hydroxy or hydroxysulfonyloxy, with proviso that when $R^1$ is hydrogen, $R^2$ is hydrogen, or a phamaceutically acceptable salt thereof. The compound can be used in a method for treating infectious diseases caused by pathogenic microorganism.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( D ) TOPOLOGY: circular ( i i ) MOLECULE TYPE: protein ( x i ) SEQUENCE DESCRIPTION: SEQ ID NO:1:

Xaa  Thr  Xaa  Xaa  Xaa  Xaa
   1                 5

NEW ANTIMICROBIAL POLYPEPTIDE COMPOUND A PHARMACEUTICAL COMPOSITION COMPRISING THE SAME, AND A METHOD FOR TREATING INFECTIOUS DISEASES

This is a continuation of application Ser. No. 07/610,759, filed Nov. 8, 1990, now abandoned.

The present invention relates to new polypeptide compound and a pharmaceutically acceptable salt thereof.

More particularly, it relates to new polypeptide compound and a pharmaceutically acceptable salt thereof, which have antimicrobial activities (especially, antifungal activities), to a process for preparation thereof, to pharmaceutical composition comprising the same, and to a method for treating infectious diseases in human being or animals.

Accordingly, one object of the present invention is to provide the polypeptide compound and a pharmaceutically acceptable salt thereof, which are highly active against a number of pathogenic microorganisms.

Another object of the present invention is to provide a process for the preparation of the polypeptide compound and a salt thereof.

A further object of the present invention is to provide a pharmaceutical composition comprising, as an active ingredient, said polypeptide compound or a pharmaceutically acceptable salt thereof.

Still further object of the present invention is to provide a method for treating infectious diseases caused by pathogenic microorganisms, which comprises administering said polypeptide compound to infected human being or animals.

The object polypeptide compound of the present invention is novel and can be represented by the following general formula [ I ] (SEQ ID NO: 1) :

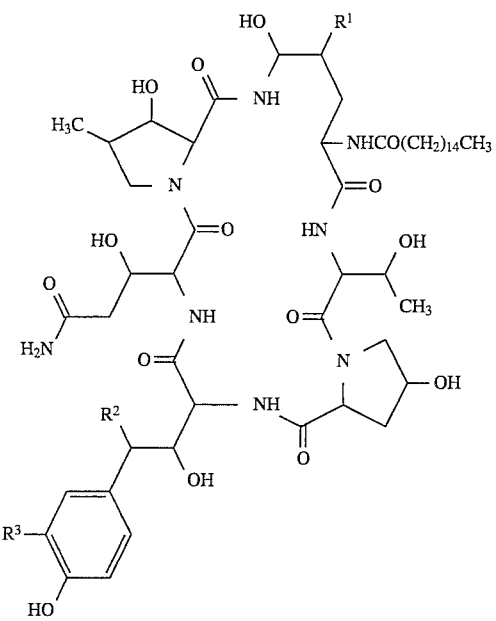

wherein $R^1$ is hydrogen or hydroxy, $R^2$ is hydrogen or hydroxy, $R^3$ is hydroxy or hydroxysulfonyloxy, with proviso that when $R^1$ is hydrogen, $R^2$ is hydrogen.

The polypeptide compound [I] (SEQ ID NO: 1) of the present invention can be prepared by the processes as illustrated in the following schemes.

Process 1 a strain belonging to the Coleophoma which is capable of producing the compound [Ia] (SEQ ID NO: 1) or a salt thereof —fermentation→

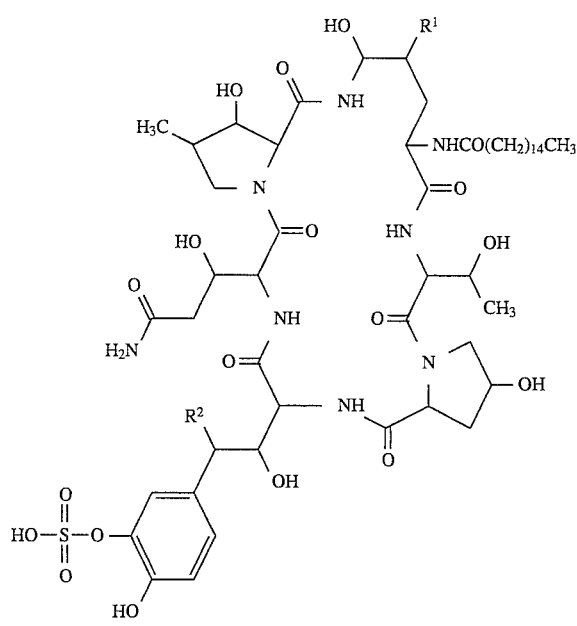

[Ia] (SEQ ID NO: 1) or a salt thereof

-continued
Process 2

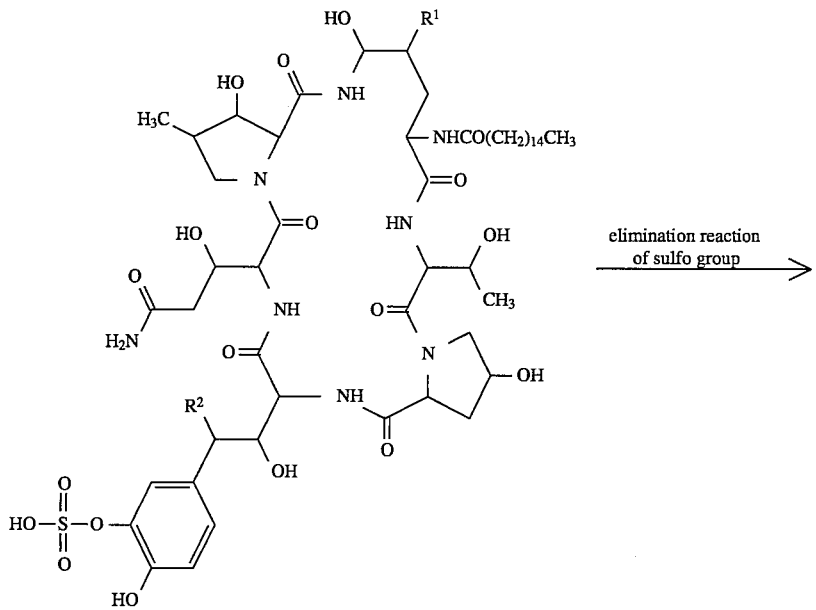

[Ia] (SEQ ID NO: 1)
or a salt thereof elimination reaction
of sulfo group
⟶

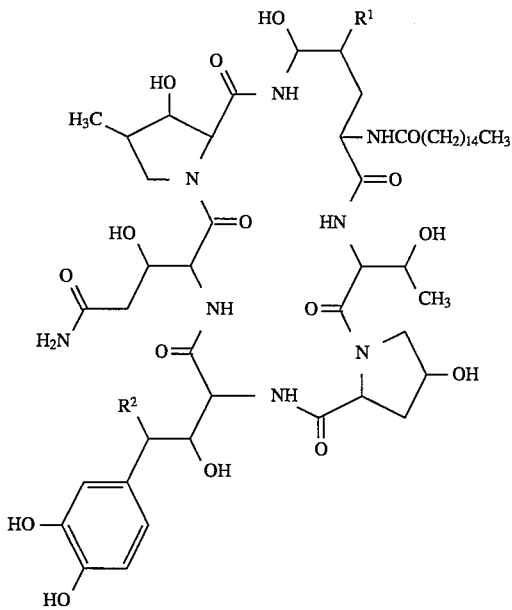

[Ib] (SEQ ID NO: 1)
or a salt thereof wherein $R^1$ and $R^2$ are each as defined above.

Suitable pharmaceutically acceptable salt of the object compound [I] (SEQ ID NO: 1) is conventional non-toxic mono or di salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspattic acid salt, glutamic acid salt, etc.], and the like.

The process for preparing the object compound [I] (SEQ ID NO: 1) or a salt thereof of the present invention is explained in detail in the following.

PROCESS 1

The object compound [Ia] (SEQ ID NO: 1) or a salt thereof can be preparedly the fermentation process.

The fermentation process is explained in detail in the following.

The compound [Ia] (SEQ ID NO: 1) or a salt thereof of this invention can be produced by fermentation of the compound [Ia] (SEQ ID NO: 1) or a salt thereof-producing strain belonging to the genus Coleophoma such as Coleophoma sp. F-11899 in a nutrient medium.

(i) Microorganism:

Particulars of the microorganism used for producing the compound [Ia] (SEQ ID NO: 1) or a salt thereof is explained in the following.

The strain F-11899 was originally isolated from a soil sample collected at Iwaki-shi, Fukushima-ken, Japan. This organism grew rather restrictedly on various culture media, and formed dark grey to brownish grey colonies. Anamorph (conidiomata) produced on a steam-sterilized leaf segment affixed on a Miura's LCA plate[1] or a corn meal agar plate by inoculating the isolate, while neither teleomorph nor anamorph formed on the agar media. Its morphological, cultural and physiological characteristics are as follows.

Cultural characteristics on various agar media are summarized in Table 1. Cultures on potato-dextrose agar grew rather rapidly, attaining 3.5–4.0 cm in diameter after two weeks at 25° C. This colony surface was plane, felty, somewhat wrinkly and brownish grey. The colony center was pale grey to brownish grey, and covered with aerial hyphae. The reverse color was dark grey. Colonies on malt extract agar grew more restrictedly, attaining 2.5–3.0 cm in diameter under the same conditions. The surface was plane, thin to felty and olive brown. The colony center was yellowish grey, and covered with aerial hyphae. The reverse was brownish grey.

The morphological characteristics were determined on basis of the cultures on a sterilized leaf affixed to a Miura's LCA plate. Conidiomata formed on the leaf segment alone. They were pycnidial, superficial, separate, discoid to ampulliform, flattened at the base, unilocular, thin-walled, black, 90–160 (-200) μm in diameter and 40–70 μm high. Ostiole was often single, circular, central, papillate, 10–30 μm in diameter and 10–20 μm high. Conidiophores formed from the lower layer of inner pycnidial walls. They were hyaline, simple or sparingly branched, septate and smooth. Conidiogenous cells were enteroblastic, phialidic, determinate, ampulliform to obpyriform, hyaline, smooth, 5–8×4–6 μm, with a collarette. The collarettes were campanulate to cylindrical, and 14–18×3–5 μm. Conidia were hyaline, cylindrical, thin-walled, aseptate, smooth and 14–16(-18)×2–3μm.

The vegetative hyphae were septate, brown, smooth and branched. The hyphal cells were cylindrical and 2–7 μm thick. The chlamydospores were absent.

The strain F-11899 had a temperature range for growth of 0° to 31° C. and an optimum temperature of 23° to 27° C. on potato dextrose agar.

The above characteristics indicate that the strain F-11899 belongs to the order Coelomycetes[2, 3, 4]. Thus, we named the strain "Coelomycetes strain F-11899".

TABLE 1

| Cultural characteristics of the strain F-11899 | |
|---|---|
| Medium | Cultural characteristics |
| Malt extract agar (Blakeslee 1915) | G: Rather restrictedly, 2.5–3.0 cm S: Circular, plane, thin to felty, olive brown (4F5), arising aerial hyphae at the center (yellowish grey (4B2) R: Brownish grey (4F2) |

TABLE 1-continued

| Cultural characteristics of the strain F-11899 | |
|---|---|
| Medium | Cultural characteristics |
| Potato dextrose agar (Difco 0013) | G: Rather rapidly, 3.5–4.0 cm S: Circular, plane, felty, somewhat wrinkly, brownish grey (4F2), arising aerial hyphae at the center (pale grey (4B1) to brownish grey (4F2) R: Dark grey (4F1) |
| Czapeck's solution agar (Raper and Thom 1949) | G: Very restrictedly, 1.0–1.5 cm S: Irregular, thin, scanty, immersed, subhyaline to white R: Subhyaline to white |
| Sabouraud dextrose agar (Difco 0109) | G: Restrictedly, 2.0–2.5 cm S: Circular, plane, thin, white, sectoring, light brown (6D5) at the colony center R: Pale yellow (4A3) |
| Oatmeal agar (Difco 0552) | G: Fairly rapidly, 4.0–4.5 cm S: Circular, plane, felty to cottony, dark grey (4F1) to brownish grey (4F2) R: Brownish grey (4D2) |
| Emerson Yp Ss agar (Difco 0739) | G: Restrictedly, 2.0–2.5 cm S: Circular to irregular, plane, felty, dark grey (4F1) to brownish grey (4F2) R: Medium grey (4E1) to dark grey (4F1) |
| Corn meal agar (Difco 0386) | G: Rather restrictedly, 2.5–3.0 cm S: Circular, plane, thin to felty, dark grey (2F1) to olive (2F3) R: Dark grey (2F1) to olive (2F3) |
| MY20 agar | G: Restrictedly, 1.5–2.0 cm S: Circular to irregular, thin, sectoring, yellowish white (4A2) R: Pale yellow (4A3) to orange white (5A2) |

Abbreviations:
G: growth, measuring colony size in diameter
S: colony surface
R: reverse These characteristics were observed after 14 days of incubation at 25° C. The color descriptions were based on the Methuen Handbook of Colour[5].

1) Miura, K. and M. Y. Kudo: An agar-medium for aquatic Hyphomycetes., Trans. Ycolo. Soc. Japan, 11:116–118, 1970.

2) Arx, J. A. von: The Genera of Fungi—Sporulating in Pure Culture (3rd ed.), 315 p., J. Cramer, Vaduz, 1974.

3) Sutton, B.C.: The Coelomycetes—Fungi Imperfecti with Pycnidia, Acervuli and Stromata., 696 p., Commonwealth Mycological Institute, Kew, 1980.

4) Hawksworth, D. L., B.C. Sutton and G. C. Ainsworth: Dictionary of the Fungi (7th ed.), 445 p., Commonwealth Mycological Institute, Kew., 1983.

5) Kornerup, A. and Wanschef, J. H.: Methuen Handbook of Colour (3rd ed.), 252 p., Methuen, London, 1983.

A culture of Coelomycetes strain F-11599 thus named has been deposited with the Fermentation Research Institute Agency of Industrial Science and Technology (1–3, Higashi 1 chome, Tsukuba-shi, IBARAKI 305 JAPAN) on Oct. 26, 1989 under the number of FERM BP-2635.

After that, however, we have further studied the classification of the strain F-11899, and have found that the strain F-11899 resembled Coleophoma empetri (Rostrup) Petrak 1929 [2, 3, 4] belonging to the order Coelomycetes, but differed in some pycnidial characteristics: globose or flattened at the base, immersed, and not papillate.

Considering these characteristics, we classified this strain in more detail and renamed it as "Coleophoma sp. F-11899".

In this connection, we have already taken step to amend the name, "Coelomycetes strain F-11899" to Coleophoma sp. F-11899 with the Fermentation Research Institute Agency of Industrial Science and Technology on Sep. 21, 1990.

(ii) Production of the compound [Ia] (SEQ ID NO: 1) or a salt thereof

The compound [Ia] (SEQ ID NO: 1) or a salt thereof of this invention is produced when the compound [Ia] (SEQ ID NO: 1) or a salt thereof-producing strain belonging to the genus Coleophoma is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, sucrose, starch, fructose or glycerin, or the like.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea or amino acid, or the like.

The carbon and nitrogen sources, though advantageously employed in combination, need not to be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, zinc salts, or cobalt salts, or the like.

If necessary, especially when the culture medium foams seriously a defoaming agent, such as liquid paraffin, fatty oil, plant oil, mineral oil or silicone, or the like may be added.

As in the case of the preferred methods used for the production of other biologically active substances in massive amounts, submerged aerobic cultural conditions are preferred for the production of the compound [Ia] (SEQ ID NO: 1) or a salt thereof in massive amounts.

For the production in small amounts, a shaking or surface culture in a flask or bottle is employed.

Further, when the growth is carried out in large tanks, it is preferable to use the vegetative form of the organism for inoculation in the production tanks in order to avoid growth lag in the process of production of the compound [Ia] (SEQ ID NO: 1) or a salt thereof. Accordingly, it is desirable first to produce a vegetative inoculum of the organism by inoculating a relatively small quantity of culture medium with spores or mycelia of the organism and culturing said inoculated medium, and then to transfer the cultured vegetative inoculum to large tanks. The medium, in which the vegetative inoculum is produced, is substantially the same as or different from the medium utilized for the production of the compound [Ia] (SEQ ID NO: 1) or a salt thereof.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 10° C. and 40° C., preferably 20° C. to 30° C., for a period of about 50 hours to 150 hours, which may be varied according to fermentation conditions and scales.

When the fermentation is completed, the culture broth is then subjected for recovery of the compound [Ia] (SEQ ID NO: 1), or a salt thereof to various procedures conventionally used for recovery and purification of biological active substances, for instance, solvent extraction with an appropriate solvent or a mixture of some solvents, chromatography or recrystallization from an appropriate solvent or a mixture of some solvents, or the like.

According to this invention, in general, the compound [Ia] (SEQ ID NO: 1) or a salt thereof is found both in the cultured mycelia and cultured broth. Accordingly, then the compound [Ia] (SEQ ID NO: 1) or a salt thereof is removed from the whole broth by means of extraction using an appropriate organic solvent such as acetone or ethyl acetate, or a mixture of these solvents, or the like.

The extract is treated by a conventional manner to provide the compound [Ia] (SEQ ID NO: 1) or a salt thereof, for example, the extract is concentrated by evaporation or distillation to a smaller amount and the resulting residue containing active material, i.e. the compound [Ia] (SEQ ID NO: 1) or a salt thereof is purified by conventional purification procedures, for example, chromatography or recrystallization from an appropriate solvent or a mixture of some solvents.

When the object compound is isolated as a salt of the compound $[I_a]$, it can be converted to the free compound $[I_a]$ or another salt of the compound $[I_a]$ according to a conventional manner.

PROCESS 2

The compound [Ib] (SEQ ID NO: 1) or a salt thereof can be prepared by subjecting the compound [Ia] (SEQ ID NO: 1) or a salt thereof to elimination reaction of sulfo group.

Suitable salt of the compound [Ib] (SEQ ID NO: 1) can be referred to the acid addition salt as exemplified for the compound [I] (SEQ ID NO: 1).

This elimination reaction is carried out in accordance with a conventional method in this field of the art such as reaction with an enzyme or the like.

The reaction with an enzyme can be carried out by reacting the compound [Ia] (SEQ ID NO: 1) or a salt thereof with an enzyme suitable for the elimination reaction of sulfo group.

Suitable example of said enzyme may include sulfatase such as sulfatase Type IV produced by Aerobacter aerogenes, or the like.

This elimination reaction is usually carried out in a solvent such as phosphate buffer, Tris-HCL buffer or any other solvent which does not adversely influence the reaction.

The reaction temperature is not critical and the reaction can be carried out at room temperature or under warming.

Biological Properties of the Compound [I]
(SEQ ID NO: 1)

As examples for showing biological activity of the compound [I] (SEQ ID NO: 1), some biological data are explained in the following.

Test 1 Antimicrobial activity (1):

Antimicrobial activity of FR901379 substance [the compound of Example 1(1)] was measured by micro-broth dilution method in 96 well multi-trays employing yeast nitrogen base dextrose medium. To a 50 µl sample solution with serial 2-fold dilutions was added a 50 µl of microorganism suspension in saline to yield a final concentration of $1 \times 10^5$ colony forming units/ml. The Candida and Aspergillus cultures were incubated at 37° C. for 22 hours, the Cryptococcus cultures were incubated at 30° C. for 48 hours. After incubation, the growth of microorganism in each well was determined by measuring the turbidity. The results were shown as $IC_{50}$ value in which concentration the turbidity was half of that in the well without sample. The results are shown in Table 2.

TABLE 2

| Organism | $IC_{50}$ |
|---|---|
| Candida albicans FP578 | <0.025 |
| Candida albicans FP582 | <0.025 |
| Candida albicans FP629 | 0.05 |
| Candida albicans FP633 | 0.025 |
| Candida krusei YC109 | 0.2 |
| Candida utilis YC123 | 0.05 |
| Candida tropicalis YC118 | 0.1 |
| Cryptococcus neoformans YC203 | >25 |
| Cryptococcus albidus YC201 | >12.5 |
| Aspergillus niger ATCC9642 | 0.05 |
| Aspergillus fumigatus FD050 | 0.8 |

Test 2 Protective effect of FR901379 substance against systemic infection of Candida albicans ICR mice (female, 4 weeks old, 5 animals per group) were intravenously injected with $2.5 \times 10^6$ Candida albicans FP633. Therapies were subcutaneously administered 1 hour after infection and once a day for three concecutive days. The results were observed at 9 days after infection. The results are shown in Table 3.

TABLE 3

| Dose (mg/kg) | survived/treated |
|---|---|
| 30 | 5/5 |
| 3 | 5/5 |
| 0.3 | 3/5 |
| 0 | 0/5 |

Test 3 Acute toxicity of FR901379 substance:

The acute toxicity of FR901379 substance was determined to ICR mice (female, 4 weeks old) by a single intraperitoneal injection. No toxic symptom was observed at the dose of 500 mg/kg.

Test 4 Antimicrobial activity (2) :

Antimicrobial activity of FR901379 substance and FR133302 substance (the compound of Example 2) were measured by the method of pulp-disc diffusion assay against Candida albicans FP633 on YNBD agar medium 37° C. for 16 hours. The results were shown below as a diameter of inhibition zone which a disc containing 2 μg of each compound exhibited. The results are shown in Table 4.

TABLE 4

| Compound | Diameter (mm) |
|---|---|
| FR901379 | 21 |
| FR133302 | 16 |

From the test results, it is realized that the polypeptide compound [I] (SEQ ID NO: 1) of the present invention has an anti-microbial activity (especially, antifungal activity).

The pharmaceutical composition of this invention can be used in the form of a pharmaceutical preparation, for example, in solid, semisolid or liquid form, which contains the polypeptide compound [I] (SEQ ID NO: 1) or a pharmaceutically acceptable salt thereof, as an active ingredient in admixture with an organic or inorganic carrier or excipient suitable for external, oral or parenteral administrations. The active ingredient may be compounded, for example, with the usual non-toxic, pharmaceutically acceptable carriers for tablets, pellets, capsules, suppositories, solutions, emulsions, suspensions, and any other form suitable for use. And, if necessary, in addition, auxiliary, stabilizing, thickening and coloring agents and perfumes may be used. The polypeptide compound [I] (SEQ ID NO: 1) or a pharmaceutical acceptable salt thereof is/are included in the pharmaceutical composition in an amount sufficient to produce the desired antimicrobial effect upon the process or condition of diseases.

For applying the composition to human, it is preferable to apply it by intravenous, intramuscular or oral administration. While the dosage of therapeutically effective amount of the polypeptide compound [I] (SEQ ID NO: 1) varies from and also depends upon the age and condition of each individual patient to be treated, in the case of intravenous administration, a daily dose of 0.01–10 mg of the polypeptide compound [I] (SEQ ID NO: 1) per kg weight of human being, in the case of intramuscular administration, a daily dose of 0.1–10 mg of the polypeptide compound [I] (SEQ ID NO: 1) per kg weight of human being, in case of oral administration, a daily dose of 0.5–50 mg of the polypeptide compound [I] (SEQ ID NO: 1) per kg weight of human being is generally given for treating infectious disease.

The following examples are given for the purpose of illustrating the present invention in more detail.

EXAMPLE 1

(1) A seed medium (160 ml) consisting of sucrose 4%, cotton seed flour 2%, dried yeast 1%, peptone 1%, $KH_2PO_4$ 0.2%, $CaCO_3$ 0.2% and Tween 80 (made by NAKARAI CHEMICALS LTD.) 0.1% was poured into each of two 500 ml Erlenmeyer flasks and sterilized at 121° C. for 30 minutes. A loopful of slant culture of Coleophoma sp. F-11899 was inoculated to each of the medium and cultured under shaking condition at 25° C. for 4 days.

A production medium (20 liters) consisting of Pine Dex #3 (made by Matsutani Chemical Ltd.) 3%, glucose 1%, wheat germ 1%, cotton seed flour 0.5%, $KH_2PO_4$ 2%, $Na_2HPO_4.12H_2O$ 1.5%, $ZnSO_4.7H_2O$ 0.001% and Adekanol (defoaming agent, made by Asahi Denka Co., Ltd.) 0.05% was poured into a 30 liter-jar fermentor and sterilized at 121° C. for 30 minutes.

The resultant seed culture broth (320 ml) was inoculated to the production medium and cultured at 25° C. for 4 days, agitated at 200 rpm and aerated at 20 liters per minute. To the cultured broth thus obtained (20 liters) was added an equal volume of acetone. After occasionally stirring at room temperature for a while, the broth was filtered. The filtrate was concentrated in vacuo to remove acetone. The aqueous filtrate (10 liters) was washed with two equal volume of ethyl acetate and extracted with n-butanol (10 liters) twice.

The combined n-butanol layer was concentrated in vacuo and the residue was applied on a column (300 ml) of Silica gel 60 (made by E. Merck) and eluted with a stepwise organic solvent mixture consisting of dichloromethane-methanol. The fractions having anti-Candida activity were eluted in the range of the solvent mixture (3:1 through 1:1). The active fractions were combined and concentrated in vacuo to dryness. The residue was dissolved in 50% aqueous methanol (15 ml) and applied on a column (250 ml) of ODS YMC GEL (made by Yamamura Chemical Lab.). The column was washed with 50% aqueous methanol and eluted with 80% aqueous methanol. The eluate was concentrated and was further purified on a centrifugal partition chromatography (CPC) using a solvent system n-butanol:methanol:water (4:1:5) of upper stationary phase and lower mobile phase in a descending mode. The pooled fractions containing the object compound (major component) were concentrated in vacuo and applied on a column (35 ml) of silica gel 60. The column was developed with n-butanol:acetic acid:water (6:1:1). The active fractions were combined and concentrated in vacuo to dryness and dissolved in a small volume of 50% aqueous methanol. The solution was passed through a column (3.5 ml) of ODS YMC GEL. The column was washed with 50% aqueous methanol and eluted with methanol. The eluate was concentrated to dryness, dissolved in a small volume of water and adjusted to pH 7.0 with 0.01N NaOH. The solution was freeze-dried to give a white powder of said compound in its sodium salt form (hereinafter referred to as FR901379 substance (SEQ ID NO: 1)) (11 mg).

The fractions containing two minor components after CPC was concentrated in vacuo and purified on a preparative high performance liquid chromatography (HPLC), column of LiChrosorb RP-18 (Trademark, made by Merck 250×ψ25 mm) using a mobile phase composed of 45% aqueous $CH_3CN$—0.5% $NH_4H_2PO_4$ at a flow rate of 9.9 ml/minute. The fraction containing one of the two components was diluted with an equal volume of water and passed through a column (1 ml) of ODS YMC Gel. The column was washed with 40% aqueous MeOH and eluted with MeOH. The eluate was concentrated in vacuo to dryness, then dissolved in a small volume of water and freeze-dried to give said component in its ammonium salt form as a white powder (2.2 mg) (hereinafter referred to as FR901381 substance).

In a similar manner, the other minor component in its ammonium salt form was obtained as a white powder (1.2 mg) (hereinafter referred to as FR901382 substance (SEQ ID NO: 1) ).

The FR901379 substance (SEQ ID NO: 1) as obtained has the following physico-chemical properties.

Appearance: white powder

Nature: neutral substance

Melting point: 215°–221° C. (dec.)

Specific rotation: $[\alpha]_D^{23}$ −20.3(C:0.5, $H_2O$)

Molecular formula: $C_{51}H_{81}N_8O_{21}SNa$

Elemental Analysis: Calcd: for $C_{51}H_{81}N_8SO_{21}Na$ C 51.17, H 6.77, N 9.36, S 2.68 (%)

Found: C 49.61, H 7.58, N 7.65, S 2.14 (%)

Molecular weight: HRFAB-MS 1219.5078 (Calcd for $C_{51}H_{82}N_8SO_{21}$+ 2Na–H: 1219.5032)

Solubility:

soluble: methanol, water slightly soluble: ethyl acetate, acetone insoluble: chloroform, n-hexane Color reaction:

positive: iodine vapor reaction, cerium sulfate reaction, ferric chloride reaction, Ninhydrin reaction negative: Dragendorff reaction, Ehrlich reaction Thin layer chromatography (TLC):

| Stationary phase | Developing solvent | Rf value |
| --- | --- | --- |
| silica gel* | n-butanol:acetic acid:water (3:1:1) | 0.36 |
|  | ethyl acetate:isopropyl alcohol:water (5:3:1) | 0.31 |

*Silica Gel 60 (made by E. Merck)

Ultraviolet absorption spectrum:

methanol λ max ($E_{1cm}^1$): 207(169), 276(13.5), 225(sh), 283(sh) nm methanol λ max+0.01N-NaOH ($E_{1cm}^1$): 209(232), 244(59.5), 284(13.5), 294(sh) nm Infrared absorption spectrum:

KBr ν max: 3350, 2920, 2840, 1660, 1625, 1530, 1510, 1435, 1270, 1240, 1070, 1045, 800, 755, 710 $cm^{-1}$ $^1$H Nuclear magnetic resonance spectrum: ($CD_3OD$, 400 MHz) δ: 7.30 (1H, d, J=2 Hz), 7.03 (1H, dd, J=8 and 2 Hz), 6.85 (1H, d, J=8 Hz), 5.23 (1H, d, J=3 Hz), 5.06 (1H, d, J=4 Hz), 4.93 (1H, d, J=3 Hz), 4.59-4.51 (3H, m), 4.47-4.35 (5H, m), 4.29 (1H, dd, J=6 and 2 Hz), 4.17 (1H, m), 4.07 (1H, m), 3.95-3.89 (2H, m), 3.76 (1H, broad d, J=11Hz), 3.36 (1H, m), 2.75 (1H, dd, J=16 and 4 Hz), 2.50 (1H, m), 2.47 (1H, dd, J=16 and 9 Hz), 2.38 (1H, m), 2.21 (2H, m), 2.03-1.93 (3H, m), 1.57 (2H, m), 1.45-1.20 (24H, m), 1.19 (3H, d, J=6 Hz), 1.08 (3H, d, J=6 Hz), 0.90 (3H, t, J=7 Hz)

From the analysis of the above physical and chemical properties, and the result of the further investigation of identification of chemical structure, the chemical structure of the FR901379 substance has been identified and assigned as follows (SEQ ID NO: 1).

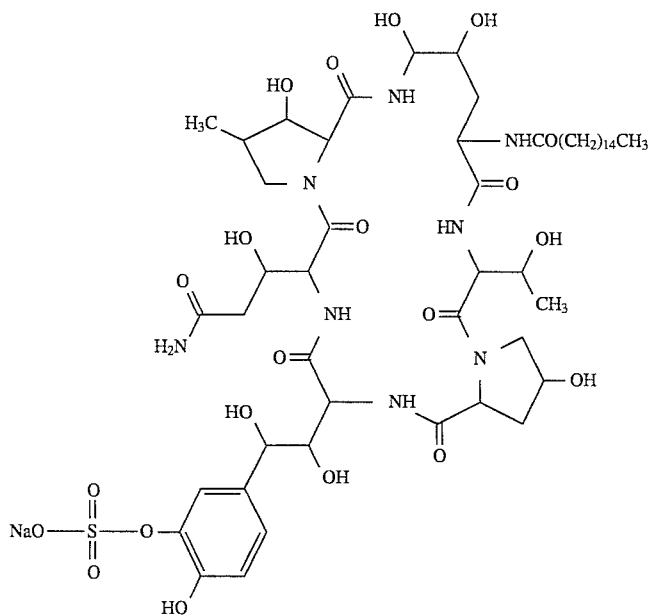

The FR901381 substance (SEQ ID NO: 1) as obtained has the following physico-chemical properties.

Appearance: white powder
Nature: neutral substance
Melting point: 218°–223° C. (dec.)
Specific rotation: $[\alpha]_D^{23}$ −10.5° (C: 0.5 MeOH)
Molecular formula: $C_{51}H_{81}N_8O_{20}S \cdot NH_4$
Molecular weight HRFAB-MS 1203.5100 (Calcd for $C_{51}H_{82}N_8O_{20}S+2Na-H$: 1203.5083)
Solubility:
soluble: methanol, ethanol
slightly soluble: water, acetone
insoluble: chloroform, n-hexane
Color reaction:
positive: iodine vapor reaction, cerium sulfate reaction
negative: Dragendorff reaction, Ehrlich reaction
Thin layer chromatography (TLC):

| Stationary phase | Developing solvent | Rf value |
|---|---|---|
| silica gel* | n-butanol:acetic acid:water (3:1:1) | 0.34 |
| | ethyl acetate:isopropyl alcohol:water (5:3:1) | 0.67 |

*Silica Gel 60 (made by E. Merck)

Ultraviolet absorption spectrum:
methanol λ max ($E_{1cm}^1$
): 206(196), 278(4), 243(sh), 284(sh) nm
methanol λ max+0.01N-NaOH ($E_{1cm}^1$
): 208(252), 290(5), 241(sh) nm Infrared absorption spectrum: KBr ν max: 3300, 2900, 2840, 1680, 1660, 1640, 1620, 1510, 1460, 1430, 1330, 1240, 1040, 960 cm$^{-1}$ $^1$H Nuclear magnetic resonance spectrum: (CD$_3$OD, 400 MHz) δ: 7.18 (1H, d, J=2 Hz), 6.90 (1H, dd, J=2 and 8.5 Hz), 6.81 (1H, d, J=8.5 Hz), 5.29 (1H, d, J=3 Hz), 5.08 (1H, d, J=3.5Hz), 4.98 (1H, d, J=3 Hz), 4.63 (1H, dd, J=7 and 11 Hz), 4.58-4.51 (3H, m), 4.46-4.38 (3H, m), 4.37 (1H, d, J=2 Hz), 4.16 (1H, dd, J=2 and 5 Hz), 4.07 (1H, dd, J=7.5 and 9.5 Hz), 4.02-3.94 (2H, m), 3.78 (1H, br d, J=11Hz), 3.38 (1H, t, J=9.5 Hz), 2.69 (1H, dd, J=4.5 and 15 Hz), 2.63-2.50 (3H, m), 2.46 (1H, m), 2.43 (1H, dd, J=9 and 15 Hz), 2.21 (2H, t, J=7.5 Hz), 2.07-1.95 (3H, m), 1.58 (2H, m), 1.29 (24H, m), 1.16 (3H, d, J=6.5 Hz), 1.07 (3H, d, J=7 Hz), 0.89 (3H, t, J=6.5 Hz)

$^{13}$C Nuclear magnetic resonance spectrum: (CD$_3$OD, 100 MHz) δ : 176.7 (s), 175.9 (s), 174.4 (s), 174.0 (s), 172.8 (s), 172.5 (s), 172.5 (s), 169.4 (s), 149.1 (s), 141.1 (s), 131.1 (s), 128.0 (d), 125.3 (d), 118.3 (d), 75.9 (d), 74.0 (d), 73.9 (d), 71.3 (d), 70.7 (d), 70.5 (d), 70.2 (d), 68.2 (d), 62.4 (d), 58.6 (d), 58.4 (d), 57.2 (t), 55.5 (d), 52.9 (t), 51.4 (d), 40.8 (t), 39.9 (t), 39.1 (d), 39.0 (t), 36.7 (t), 35.0 (t), 33.1 ( t), 30.8 (t×5), 30.7 (t), 30.7 (t), 30.5 (t), 30.4 (t), 30.3 (t), 27.0 (t), 23.7 (t), 19.5 (q), 14.4 (q), 11.1 (q)

From the analysis of the above physical and chemical properties, and the result of the further investigation for identification of chemical structure, the chemical structure of the FR901381 substance has been identified and assigned as follows (SEQ ID NO: 1).

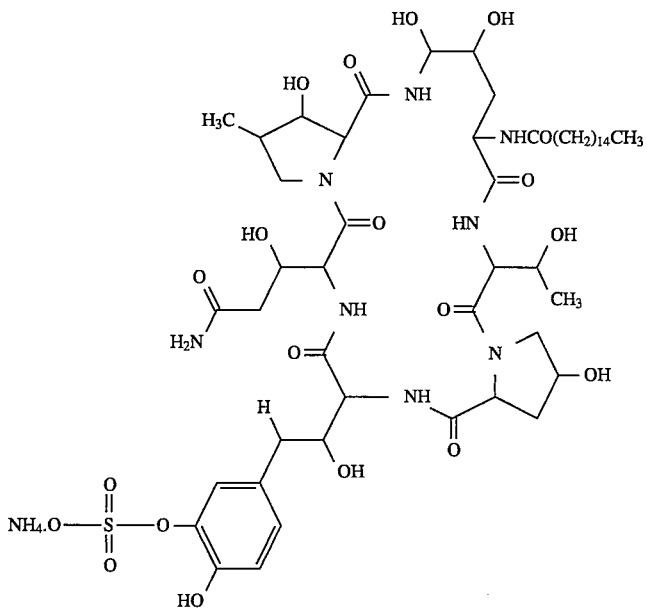

The FR901382 substance (SEQ ID NO: 1) as obtained has the following physico-chemical properties.

Appearance: white powder
Nature: neutral substance
Melting point: 208°–217° C. (dec.)
Specific rotation: $[\alpha]_D^{23}$ − 9.4° (C: 0.5, MeOH)
Molecular formula: $C_{51}H_{81}N_8O_{19}S \cdot NH_4$
Molecular weight: HRFAB-MS 1187.5139 (Calcd. for $C_{51}H_{82}N_8O_{19}S+2Na-H$ 1187.5134)
Solubility:
soluble: methanol, ethanol
slightly soluble: water, acetone
insoluble: chloroform, n-hexane
Color reaction:
positive: iodine vapor reaction, cerium sulfate reaction
negative: Dragendorff reaction, Ehrlich reaction
Thin layer chromatography (TLC):

| Stationary phase | Developing solvent | Rf value |
|---|---|---|
| silica gel* | n-butanol:acetic acid: water (3:1:1) | 0.43 |
|  | ethyl acetate:isopropyl alcohol:water (5:3:1) | 0.9 |

*Silica Gel 60 (made by E. Merck)

Ultraviolet absorption spectrum:
methanol λ max ($E_{1cm}^1$): 205(180), 276(13), 224(sh), 283(sh) nm
methanol λ max+0.01N-NaOH ($E_{1cm}^1$): 208(262), 281(12), 1% 241(sh), 295(sh) nm Infrared absorption spectrum: KBr ν max: 3350, 2900, 2840, 1680, 1660, 1640, 1620, 1510, 1430, 1330, 1245, 1080, 1040, 960 cm$^{-1}$ $^1$H Nuclear magnetic resonance spectrum: (CD$_3$OD, 400 MHz) δ: 7.18 (1H, d, J=2 Hz), 6.90 (1H, dd, J=2 and 8.5 Hz), 6.80 (1H, d, J=8.5 Hz), 5.37 (1H, dd, J=3 and 11 Hz), 5.08 (1H, d, J=3.5 Hz), 5.00 (1H, d, J=3 Hz), 4.61 (1H, dd, J=7 and 11 Hz), 4.59 (1H, d, J=2 Hz), 4.58-4.52 (2H, m), 4.46-4.35 (3H, m), 4.29 (1H, d, J=2 Hz), 4.12 (1H, dd, J=2 and 4.5 Hz), 4.07 (1H, dd, J=8 and 9.5 Hz), 4.01 (1H, dd, J=3 and 11 Hz), 3.77 (1H, br d, J=11 Hz), 3.37 (1H, t, J=9.5 Hz), 2.69 (1H, dd, J=4.5 and 15.5 Hz), 2.63-2.50 (3H, m), 2.45 (1H, m), 2.43 (1H, dd, J=9 and 15.5 Hz), 2.24 (2H, m), 2.09-1.95 (3H, m), 1.76-1.66 (2H, m), 1.59 (2H, m), 1.29 (24H, m), 1.15 (3H, d, J=6.5 Hz), 1.06 (3H, d, J=7 Hz), 0.89 (3H, t, J=7 Hz)

$^{13}$C Nuclear magnetic resonance spectrum: (CD$_3$OD, 100 MHz) δ: 176.7 (s), 176.0 (s), 175.1 (s), 174.0 (s), 172.8 (s), 172.6 (s), 172.5 (s), 169.1 (s), 149.1 (s), 141.1 (s), 131.1 (s), 128.1 (d), 125.3 (d), 118.2 (d), 76.1 (d), 74.0 (d), 71.8 (d), 71.3 (d), 70.5 (d), 70.3 (d), 68.3 (d), 62.5 (d), 58.5 (d), 58.2 (d), 57.2 (t), 55.4 (d), 52.9 (t), 52.1 (d), 40.8 (t), 39.8(t), 39.1 (d), 38.9 (t), 36.8 (t), 33.1 (t), 30.9 (t), 30.8 (t×5), 30.7 (t), 30.7 (t), 30.5 (t), 30.4 (t), 30.3 (t), 27.3 (t), 26.9 (t), 23.7 (t), 19.4 (q), 14.4 (q), 11.1 (q)

From the analysis of the above physical and chemical properties, and the result of the further investigation for identification of chemical structure, the chemical structure of the FR901382 substance has been identified and assigned as follows (SEQ ID NO: 1).

EXAMPLE 2

To a solution of FR901379 substance (SEQ ID NO: 1) (60 mg) in 50 mM Tris-HCl buffer (pH 7.1, 30 ml) was added sulfatase (200 U) Type VI from Aerobacter aerogenes (SIGMA.NOS-1629). After incubating at 37° C. for 30 hours, desulfonated FR901379 substance (hereinafter referred to as FR133302 substance) formed was extracted with a equal volume of n-butanol and washed once with water. The extract was concentrated in vacuo and applied on a column of LiChroprep RP-18 (40–63 μm) pre-packed size B (made by Merck) equilibrated with 47% aqueous acetonitrile containing 0.5% $NH_4H_2PO_4$ and developed with the same solution. The fraction containing FR133302 substance was diluted with the equal volume of water and directly passed through a column of ODS YMC GEL (made by Yamamura Chemical Lab.). The column was washed with water and eluted with methanol. The eluate was evaporated in vacuo to remove methanol and freeze-dried to give a white powder of FR133302 substance (SEQ ID NO: 1) (26 mg).

The FR133302 substance (SEQ ID NO: 1) as obtained has the following physico-chemical properties.

Appearance: white powder

Nature: neutral substance

Melting point: 218°–222° C. (dec.)

Specific rotation: $[\alpha]_D^{22}$ −30° (C: 1.0, MeOH)

Molecular formula: $C_{51}H_{82}N_8O_{18}$

Molecular weight: HRFAB-MS 1117. 5659 (Calcd. for $C_{51}H_{82}N_8O_{18}$+Na 1117. 5645)

Solubility:

soluble: methanol, ethanol slightly soluble: water, ethyl acetate insoluble: chloroform, n-hexane Color reaction:

positive: iodine vapor reaction, cerium sulfate reaction negative: Dragendorff reaction, Molish reaction Thin layer chromatography (TLC):

| Stationary phase | Developing solvent | Rf value |
|---|---|---|
| silica gel* | n-butanol:acetic acid:water (6:1:1) | 0.35 |

*Silica Gel 60 (made by E. Merck)

Ultraviolet absorption spectrum:

methanol λ max ($E_{1cm}^1$): 207(353), 282(25), 232(sh) nm methanol λ max+0.01N-NaOH ($E_{1cm}^1$): 208(462), 246(54.5), 293(31.2)nm Infrared absorption spectrum:

KBr ν max: 3350, 2925, 2855, 1660, 1630, 1530, 1445, 1285, 1250, 1065 cm $^1$H Nuclear magnetic resonance spectrum: (CD$_3$OD, 400 MHz) δ: 6.79 (1H, d, J=2 Hz), 6.71 (1H, d, J=8 Hz), 6.61 (1H, dd, J=8 and 2 Hz), 5.25 (1H, d, J=2.5 Hz), 5.06 (1H, d, J=4 Hz), 4.96 (1H, d, J=3 Hz), 4.60-4.20 (9H, m), 4.15 (1H, m), 4.08 (1H, m), 3.99 (1 H, m), 3.91 (1H, m), 3.77 (1H, m), 3.34 (1H, m), 2.80 (1H, dd, J=15 and 3 Hz), 2.54-2.40 (3H, m), 2.20 (2H, t, J=7 Hz), 2.05-1.96 (3H, m), 1.56 (2H, m), 1.35-1.20 (24H, m), 1.15 (3H, d, J=6 Hz), 1.02 (3H, d, J=7 Hz), 0.89 (3H, t, J=7 Hz)

$^{13}$C Nuclear magnetic resonance spectrum: (CD$_3$OD, 100 MHz) δ: 177.2 (s), 175.8 (s), 174.5 (s), 173.4 (s), 172.7 (s), 172.6 (s), 172.5 (s), 169.1 (s), 146.4 (s), 146.3 (s), 133.7 (s), 120.1 (d), 116.2 (d), 115.3 (d), 76.9 (d), 75.9 (d), 75.8 (d), 74.0 (d), 71.3 (d), 70.6 (d), 70.6 (d), 70.1 (d), 68.2 (d), 62.5 (d), 58.4 (d), 57.1 (t), 56.4 (d), 55.6 (d), 53.0 (t), 51.5 (d), 39.5 (t), 39.0 (d), 38.5 (t), 36.7 (t), 34.8 (t), 33.1 (t), 30.8 (t x 5), 30.7 (t), 30.6 (t), 30.5 (t), 30.4 (t), 30.3 (t), 26.9 (t), 23.7 (t), 19.7 (q), 14.4 (q), 11.1 (q)

The chemical structure of the FR133302 substance is as follows (SEQ ID NO: 1).

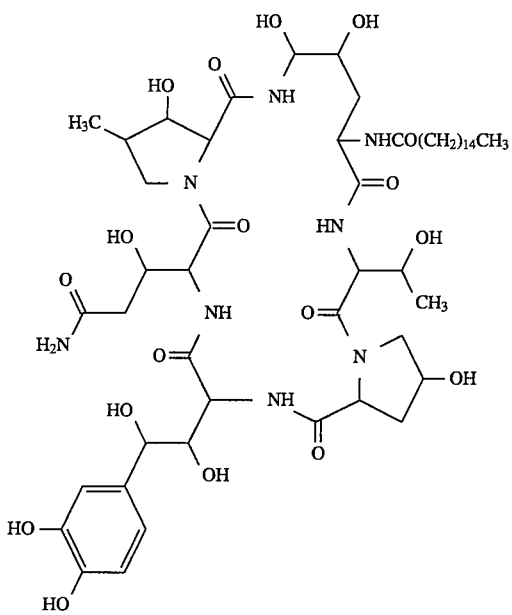
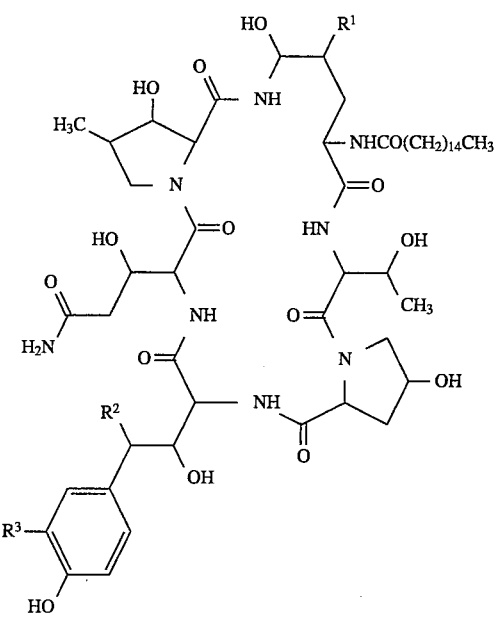

What we claim is:

1. A compound of the following general formula (SEQ ID NO: 1):

wherein $R^1$ is hydrogen or hydroxy, $R^2$ is hydrogen or hydroxy, $R^3$ is hydroxy or hydroxysulfonyloxy, with proviso that when $R^1$ is hydrogen, $R^2$ is hydrogen, or a pharmaceutically acceptable salt thereof.

2. A polypeptide compound of claim 1, wherein $R^1$ and $R^2$ are each hydroxy, and $R^3$ is hydroxysulfonyloxy.

3. A pharmaceutical composition which comprises, as an active ingredient, a compound of claim 1 or a pharmaceutically acceptable salt thereof in admixture with pharmaceutically acceptable carriers.

* * * * *

UNITED STATES PATENT AND TRADEMARK OFFICE
CERTIFICATE OF CORRECTION

PATENT NO. : 5,502,033
DATED : March 26, 1996
INVENTOR(S) : Toshiro IWAMOTO et al.

It is certified that error appears in the above-indentified patent and that said Letters Patent is hereby corrected as shown below:

On the title page, Item [54], and in Column 1, lines 1-6, the title is incorrect. It should read:

--[54]  ANTIMICROBIAL POLYPEPTIDE COMPOUND, A PHARMACEUTICAL COMPOSITION COMPRISING THE SAME, AND A METHOD FOR TREATING INFECTIOUS DISEASES--

Signed and Sealed this

Thirtieth Day of July, 1996

Attest:

BRUCE LEHMAN

*Attesting Officer*   *Commissioner of Patents and Trademarks*